United States Patent
Park et al.

(10) Patent No.: US 11,172,838 B2
(45) Date of Patent: Nov. 16, 2021

(54) SENSING BODY INFORMATION APPARATUS FOR VOLUME AND BLOOD FLOW VIA LIGHT REFLECTANCE

(71) Applicant: SAMSUNG ELECTRONICS CO., LTD., Suwon-si (KR)

(72) Inventors: Sang-bae Park, Cheongju-si (KR); Sang-hoon Lee, Incheon (KR); Jae-hoon Jeong, Suwon-si (KR); Kyung-sun Cho, Seoul (KR); Seong-seol Hong, Yongin-si (KR); Dong-jin Lee, Suwon-si (KR); Mi-jin Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1246 days.

(21) Appl. No.: 14/617,442

(22) Filed: Feb. 9, 2015

(65) Prior Publication Data

US 2015/0238098 A1    Aug. 27, 2015

(30) Foreign Application Priority Data

Feb. 24, 2014    (KR) .................. 10-2014-0021450

(51) Int. Cl.
*A61B 5/026*     (2006.01)
*A61B 5/02*      (2006.01)
(Continued)

(52) U.S. Cl.
CPC ............ *A61B 5/0261* (2013.01); *A61B 5/024* (2013.01); *A61B 5/02007* (2013.01);
(Continued)

(58) Field of Classification Search
CPC ..... A61B 5/0261; A61B 5/6844; A61B 5/024; A61B 5/742; A61B 5/02007; A61B 5/1073; A61B 5/02416; A61B 5/0077
See application file for complete search history.

(56) References Cited

U.S. PATENT DOCUMENTS 7,728,905 B2    6/2010    Tanaka et al.
7,777,808 B2    8/2010    Matsuo et al.
(Continued)

FOREIGN PATENT DOCUMENTS

CN    101030252 A    9/2007
CN    101460097 A    6/2009
(Continued)

OTHER PUBLICATIONS

"Time of Flight Camera", Peacock Technology Ltd., URL: http://www.peacocktech.co.uk/case-studies/time-of-flight-camera/, Accessed May 23, 2014, 1 page.

(Continued)

*Primary Examiner* — Serkan Akar
(74) *Attorney, Agent, or Firm* — Sughrue Mion, PLLC

(57) ABSTRACT

An apparatus and method for sensing body information is provided. The apparatus includes: a light-emitting device configured to emit a light signal toward an object that is to be sensed; a light-receiving device configured to detect a reflected light signal reflected from the object; an image sensor configured to detect the reflected light signal reflected from the object; and a controller configured to selectively drive at least one of the light-receiving device and the image sensor according to a distance between the object and the light-emitting device and to sense volume information or blood flow information of the object by using the reflected light signal.

7 Claims, 21 Drawing Sheets

(51) Int. Cl.
  *A61B 5/00*    (2006.01)
  *A61B 5/107*   (2006.01)
  *A61B 5/024*   (2006.01)

(52) U.S. Cl.
  CPC .......... *A61B 5/1073* (2013.01); *A61B 5/6844* (2013.01); *A61B 5/742* (2013.01); *A61B 5/0077* (2013.01); *A61B 5/02416* (2013.01)

(56) References Cited

U.S. PATENT DOCUMENTS

| | | | |
|---|---|---|---|
| 8,285,003 B2 | 10/2012 | Fujii et al. | |
| 8,369,575 B2 | 2/2013 | Kim | |
| 2004/0054270 A1* | 3/2004 | Pewzner | A61B 5/14546 600/341 |
| 2006/0058683 A1* | 3/2006 | Chance | A61B 5/0062 600/476 |
| 2007/0205357 A1 | 9/2007 | Tanaka et al. | |
| 2007/0206099 A1 | 9/2007 | Matsuo et al. | |
| 2009/0202113 A1 | 8/2009 | Fujii et al. | |
| 2013/0179162 A1 | 7/2013 | Merschon et al. | |
| 2013/0323673 A1 | 12/2013 | Hakomori et al. | |
| 2013/0331710 A1* | 12/2013 | Li | A61B 5/14551 600/479 |
| 2015/0038811 A1* | 2/2015 | Asaka | A61B 5/0042 600/324 |
| 2015/0173618 A1* | 6/2015 | Kusukame | A61B 5/4064 600/473 |
| 2016/0066791 A1* | 3/2016 | Wood | A61B 5/0062 600/476 |

FOREIGN PATENT DOCUMENTS

| | | |
|---|---|---|
| EP | 2281503 A2 | 2/2011 |
| JP | 2003-510121 A | 3/2003 |
| JP | 2010061294 A | 3/2010 |
| JP | 2013-143148 A | 7/2013 |
| KR | 10-2005-0065995 A | 6/2005 |
| KR | 10-2007-0090775 A | 9/2007 |
| KR | 10-2009-0101557 A | 9/2009 |
| KR | 10-2011-0121394 A | 11/2011 |
| WO | 01/22870 A1 | 4/2001 |
| WO | 2013001265 A2 | 1/2013 |
| WO | 2013019904 A2 | 2/2013 |

OTHER PUBLICATIONS

Communication dated Jul. 23, 2015, issued by the European Patent Office in counterpart European Application No. 15156119.8.
Communication dated Nov. 6, 2018, issued by the Japanese Patent Office in counterpart Japanese Application No. 2015-029826.
Communication dated Dec. 28, 2018, issued by the Chinese Patent Office in counterpart Chinese Application No. 201510084838.8.
Communication dated Jul. 9, 2019 issued by the Japanese Patent Office in counterpart Japanese Application No. 2015-029826.
Communication dated Jun. 18, 2019, issued by the European Patent Office in counterpart European Application No. 15156119.8.
Communication dated Jul. 31, 2020 issued by the Korean Intellectual Property Office in Korean Application No. 10-2014-0021450.

* cited by examiner

SENSING BODY INFORMATION APPARATUS FOR VOLUME AND BLOOD FLOW VIA LIGHT REFLECTANCE

CROSS-REFERENCE TO RELATED APPLICATION

This application claims priority under 35 U.S.C. § 119 from Korean Patent Application No. 10-2014-0021450, filed on Feb. 24, 2014, in the Korean Intellectual Property Office, the disclosure of which is incorporated herein by reference in its entirety.

BACKGROUND

1. Field

Apparatuses and methods consistent with exemplary embodiments relate to sensing body information, and more particularly, to providing an apparatus and method for sensing body information to acquire voluptuousness information and blood flow information of a body.

2. Description of the Related Art

Due to an increase in aging populations and the development of technologies, various types of medical devices have been provided for users to use in their homes. For example, representative medical devices for homes include devices for measuring a blood sugar level, for measuring a blood pressure, etc. The medical devices may help to manage the health of a user through a portable terminal such as a smartphone or the like. In particular, demands for medical devices for use in homes have been gradually increased according to needs of people for leading healthy and affluent lives.

Existing devices that measure a heart rate or blood flow information of a human use a transmission type detection method or a reflection type detection method using an infrared (IR) sensor. According to the transmission type detection method, if a light source irradiates light onto a finger, blood, bones, or tissues absorb the light, and the other portion of the light passes through the blood, the bones, or the tissues and then reaches a light receiver. An absorption degree of the light changes with respect to the blood flow due to the heartbeat, in proportion to the amount of skin, tissues, and blood that is positioned within the path of the light. Therefore, the absorption degree of the light is proportional to the blood flow. Since the light receiver receives transmitted light from which an amount of light absorbed into the finger is subtracted, variations in amount of the transmitted light reflects variations in the blood flow. Therefore, a measurement of an amount of light by the light receiver enables a detection of variations in an amount of blood flow synchronized with the heartbeat. According to the reflection type detection method, a similar blood flow variation detecting method to that of the transmission type detection method is used, but a position of the sensor receiving the light is different from that in the transmission type detection method. In the transmission type detection method, the light-receiving device is installed on a light-emitting device, such that a user's finger is placed between the light-emitting device and the light-receiving device. In the reflection type detection method, the light-receiving device is installed beside the light-emitting device to detect a reflected amount of light with respect to variations in the blood flow in order to measure the heartbeat.

There is also an existing device that measures a user's voluptuousness using a 3-dimensional (3D) body scanner. However, 3D body scanners are very expensive, and it is difficult to install and use a 3D body scanner in the home. Therefore, there is an existing device that measures voluptuousness by measuring a depth of the user through a depth camera and an image processing algorithm and then calculates the voluptuousness. The depth camera uses a time of flight (TOF) method or a pattern method. The TOF method is the most typical and basic distance measuring method and measures a difference between a time when pulses are emitted and a time when reflected waves are received in order to acquire a distance. Therefore, the TOF method is mainly used in conjunction with radar or an ultrasonic sensor. The pattern method calculates a depth by sensing intervals between IR patterns or deformations and sizes of the IR patterns.

As described above, a device that measures blood flow information such as a heartbeat or the like of a user and a device that measures voluptuousness such as a body size, body fat, or the like of the user acquires body information of the user by using IR light. Therefore, the two devices use similar methods but are installed separately from each other.

SUMMARY

One or more exemplary embodiments may address at least the above problems and/or disadvantages and other disadvantages not described above. Also, the exemplary embodiments are not required to overcome the disadvantages described above, and an exemplary embodiment may not overcome any of the problems described above.

The exemplary embodiments provide an apparatus and method for sensing body information to acquire voluptuousness information at long and short distances and acquire blood information at a closest distance.

According to an aspect of an exemplary embodiment, there is provided an apparatus for sensing body information. The apparatus may include: a light-emitting device configured to emit light to an object that is to be sensed; a light-receiving device configured to detect reflected light reflected from the object; an image sensor configured to detect the reflected light reflected from the object; and a controller configured to selectively drive at least one of the light-receiving device and the image sensor according to a distance between the object and the light-emitting device to acquire the reflected light and sense volume information or blood flow information of the object by using the reflected light.

The controller may sense the blood flow information of the object in response to the distance between the object and the light-emitting device being within a first distance and sense the volume information of the object in response to the distance between the object and the light-emitting device exceeding the first distance.

The controller may sense the blood flow information by using the light-receiving device in response to the distance between the object and the light-emitting device being within the first distance and sense the volume information by using one of the light-receiving device and the image sensor in response to the distance between the object and the light-emitting device exceeding the first distance.

The controller may sense volume information about an area of the object in response to the distance between the object and the light-emitting device exceeding the first distance and being within a second distance and sense volume information about a whole area of the object by using the image sensor in response to the distance between the object and the light-emitting device exceeding the first and second distances.

The controller may activate the image sensor to sense a saturation of the reflected light and selectively selects at least one of the light-receiving device and the image sensor according to a size of the saturation. The saturation may vary according to the distance between the object and the light-emitting device.

The light-emitting device, the light-receiving device, and the image sensor may be integrated into one sensor module. The image sensor may be disposed in center of the sensor module, a plurality of light-emitting devices may be disposed in a peripheral area of the image sensor, and a plurality of the light-receiving devices may be disposed to be paired with the light-emitting devices.

The apparatus may further include a transparent display configured to cover the sensor module to transmit the light signal and the reflected light. The controller may display at least one of the blood flow information and the volume information on the transparent display.

The blood flow information may include heart rate information and artery hardening information, and the volume information may include at least one of a body image, weight information, body circumference information, and a body mass index (BMI) value of the object. The controller may control the transparent display to display at least one of the heart rate information, the artery hardening information, and the body image, the weight information, the body circumference information, and the BMI value of the object.

In response to a user touching the transparent display, the controller may determine that the distance between the object and the light-emitting device may be within the first distance to sense the blood information of the object.

The apparatus may further include a communicator configured to communicate with an external display apparatus. The controller may transmit one of the volume information and the blood flow information to the external display apparatus.

According to an aspect of another exemplary embodiment, there is provided a method of sensing body information. The method may include: determining a distance between an object that is to be sensed and a light-emitting device that emits light to the object; selectively driving at least one of a light-receiving device and an image sensor to detect reflected light reflected from the object according to the distance between the object and the light-emitting device in order to acquire the reflected light; and sensing volume information and blood flow information of the object by using the reflected light.

In response to the distance between the object and the light-emitting device being within a first distance, the blood flow information of the object may be sensed, and in response to the distance between the object and the light-emitting device being exceeding, the volume information of the object may be sensed.

In response to the distance between the object and the light-emitting device being with the first distance, the blood flow information may be sensed by using the light-receiving device, and in response to the distance between the object and the light-emitting device exceeding the first distance, the volume information may be sensed by using one of the light-receiving device and the image sensor.

In response to the distance between the object and the light-emitting device exceeding the first distance and being within a second distance, volume information about an area of the object may be sensed by using the light-receiving device, and in response to the distance between the object and the light-emitting device exceeding the first and second distances, volume information about a whole area of the object may be sensed by using the image sensor.

The image sensor may be activated to sense a saturation of the reflected light, and the distance between the object and the light-emitting device may be determined according to a size of the saturation.

The light-emitting device, the light-receiving device, and the image sensor may be integrated into one sensor module. The image sensor may be disposed in center of the sensor module, a plurality of light-emitting devices may be disposed in a peripheral area of the image sensor, and a plurality of the light-receiving devices may be disposed to be paired with the light-emitting devices.

The method may further include: displaying at least one of the blood flow information and the volume information on a transparent display.

The blood flow information may include heart rate information and artery hardening information, and the volume information may include at least one of a body image, weight information, body circumference information, and a BMI value of the object. At least one of the heart rate information, the artery hardening information, and the body image, the weight information, the body circumference information, and the BMI value of the object may be displayed on the transparent display.

In response to a hand of a user touching the transparent display, the distance between the object and the light-emitting device may be determined as being within the first distance.

The method may further include: transmitting one of the volume information and the blood flow information to an external display apparatus.

According to an aspect of another exemplary embodiment, there is provided an apparatus for sensing body information. The apparatus may include: at least one light-emitting device configured to emit light to an object that is to be sensed; at least one light-receiving device configured to detect reflected light reflected from the object; an image sensor configured to detect the reflected light reflected from the object; and a controller configured to selectively operate in one of a first operation mode for sensing blood flow information of the object by using the light-receiving device, a second operation mode for sensing volume information of the object by using the light-receiving device, and a third operation mode for sensing the volume information of the object by using the image sensor.

BRIEF DESCRIPTION OF THE DRAWINGS

The above and/or other exemplary aspects and advantages will be more apparent by describing certain exemplary embodiments with reference to the accompanying drawings, in which.

DETAILED DESCRIPTION OF THE EXEMPLARY EMBODIMENTS

Figure 1:
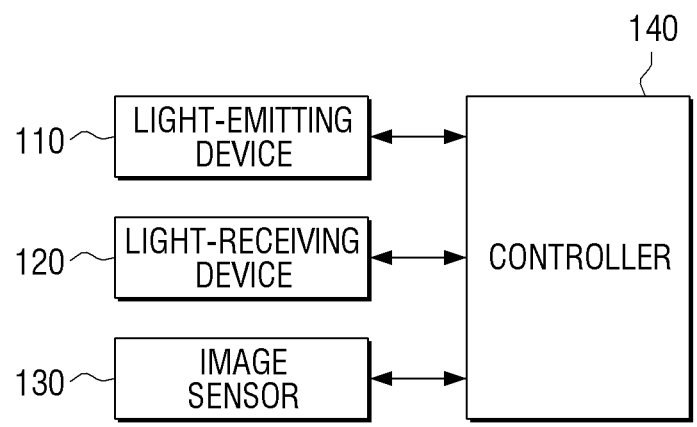
FIG. 1 is a block diagram illustrating a structure of an apparatus for sensing body information, according to an exemplary embodiment.

Exemplary embodiments are described in greater detail with reference to the accompanying drawings.

In the following description, the same drawing reference numerals are used for the same elements even in different drawings. The matters defined in the description, such as detailed construction and elements, are provided to assist in a comprehensive understanding of the exemplary embodiments. Thus, it is apparent that the exemplary embodiments can be carried out without those specifically defined matters. Also, well-known functions or constructions are not described in detail since they would obscure the exemplary embodiments with unnecessary detail.

FIG. 1 is a block diagram briefly illustrating a structure of an apparatus 100 for sensing body information, according to an exemplary embodiment. Referring to FIG. 1, the apparatus 100 includes a light-emitting device 110, a light-receiving device 120, an image sensor 130, and a controller 140.

The light-emitting device 110 emits a light signal to an object (e.g., a body or the like) that is to be sensed. Here, the light-emitting device 110 may emit an infrared (IR) light signal, but this is only exemplary. Therefore, the light-emitting device 100 may emit other types of light signals.

The light-receiving device 120 detects light reflected from the object under control of the controller 140. Here, the light-receiving device 120 may be disposed to be paired with the light-emitting device 110.

Under control of the controller 140, the image sensor 130 detects light reflected from the object. Here, the light-emitting device 110, the light-receiving device 120, and the image sensor 130 may be integrated into one sensor module. Also, the image sensor 130 may be disposed in the center of the sensor module, and a plurality of light-emitting devices 110 and a plurality of light-receiving devices 120 may be disposed in a peripheral area of the image sensor 130.

The controller 140 may selectively drive at least one of the light-receiving device 120 and the image sensor 130, according to a distance between the object and the light-emitting device 110, to acquire a reflected light signal and sense voluptuousness information and/or blood flow information of the object by using the reflected light signal.

In detail, the controller 140 may determine the distance between the object and the light-emitting device 110. Here, the controller 140 may activate the image sensor 130 to sense a saturation of the reflected light signal and determine the distance between the object and the light-emitting device 110 according to an amount of the saturation. In detail, if the saturation of the reflected light signal sensed by the image sensor 130 is higher than or equal to a preset first value, the controller 140 may determine the distance between the object and the light-emitting device 110 as a first distance. If the saturation of the reflected light signal sensed by the image sensor 130 is lower than the preset first value or is higher than or equal to a preset second value, the controller 140 may determine that the distance between the object and the light-emitting device 110 exceeds a first distance and is shorter than or equal to a second distance. Also, if the saturation of the reflected light signal sensed by the image sensor 130 is lower than the preset second value, the controller 140 may determine that the distance between the object and the light-emitting device 100 exceeds the second distance.

Also, the controller 140 may drive one of the light-receiving device 120 and the image sensor 130 according to the distance between the object and the light-emitting device 110 to sense one of the voluptuousness information and the blood flow information of the object. In detail, if the distance between the object and the light-emitting device 110 is within the first distance, the controller 140 may sense the blood flow information of the object. If the distance between the object and the light-emitting device 110 exceeds the first distance, the controller 140 may sense the voluptuousness information of the object. Here, if the distance between the object and the light-emitting device 110 is within the first distance, the controller 140 may sense the blood information by using the light-receiving device 120. If the distance between the object and the light-emitting device 100 exceeds the first distance, the controller 140 may sense the voluptuousness information by using one of the light-receiving device 120 and the image sensor 130. A method of sensing the voluptuousness information of the object will now be described in more detail. If the distance between the object and the light-emitting device 110 exceeds the first distance and is within the second distance, the controller 140 may sense the voluptuousness information of an area (e.g., a face, a lower body, or the like) of the object by using the light-receiving device 120. If the distance between the object and the light-emitting device 110 exceeds the first and second distances, the controller 140 may sense the whole voluptuousness information of the object by using the image sensor 130.

Therefore, through the apparatus 100 for sensing the body information as described above, a user may simultaneously acquire blood flow information and voluptuousness information to perform a comprehensive health assessment of the user.

Figure 2A:
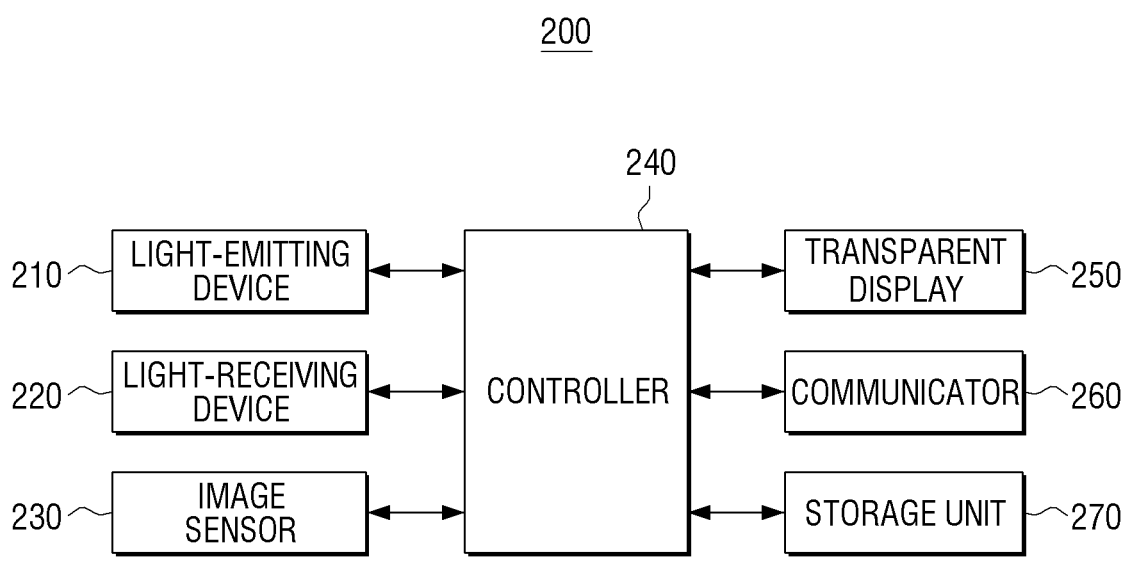
FIGS. 2A through 2C are views illustrating a structure of an apparatus for sensing body information in detail, according to an exemplary embodiment.
Figure 2B:
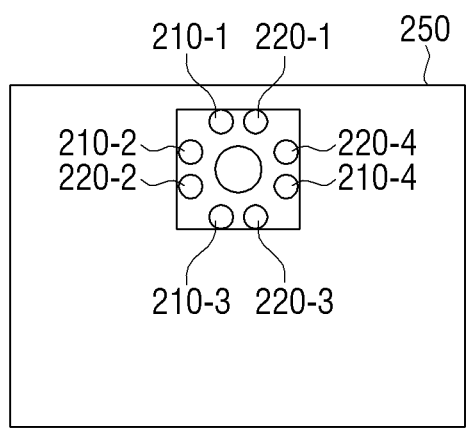
Figure 2C:
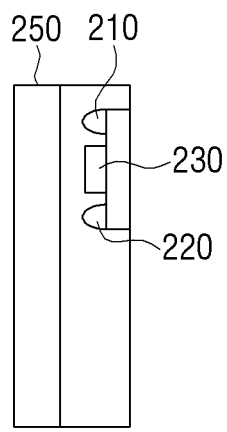

An apparatus 200 for sensing body information will now be described in more detail with reference to FIGS. 2A through 7B. FIG. 2 is a block diagram illustrating a structure of the apparatus 200 for sensing body information, according to an exemplary embodiment. Referring to FIG. 2A, the apparatus 200 includes a light-emitting device 210, a light-receiving device 220, an image sensor 230, a controller 240, a transparent display 250, a communicator 260, and a storage unit 270.

The light-emitting device 210 emits a light signal to an object that is to be sensed, to acquire body information of the object. Here, the light signal may be an IR light signal, but this is merely exemplary. Therefore, other types of light signals (e.g., visible light, etc.) or an ultrasonic wave may be used.

The light-receiving device 220 detects reflected light acquired by reflecting the light signal emitted from the light-emitting device 210 from the object. The light-receiving device 200 may be disposed to be paired with the light-emitting device 210. In an operation mode in which the light-receiving device 220 is driven, the light-emitting device 210 and the light-receiving device 220 may sequentially operate to acquire volume information about an area of the object.

The image sensor 230 detects the reflected light that is acquired by reflecting the light signal emitted from the light-emitting device 210 from the object. Also, in an operation mode in which the image sensor 230 is driven, the image sensor 230 may acquire the reflected light to acquire volume information about a whole area of the object. The image sensor 230 may also detect a saturation of the reflected light acquired by reflecting the light signal emitted from the light-emitting device 210 from the object in order to measure a distance between the object and the light-emitting device 210.

Figure 3:
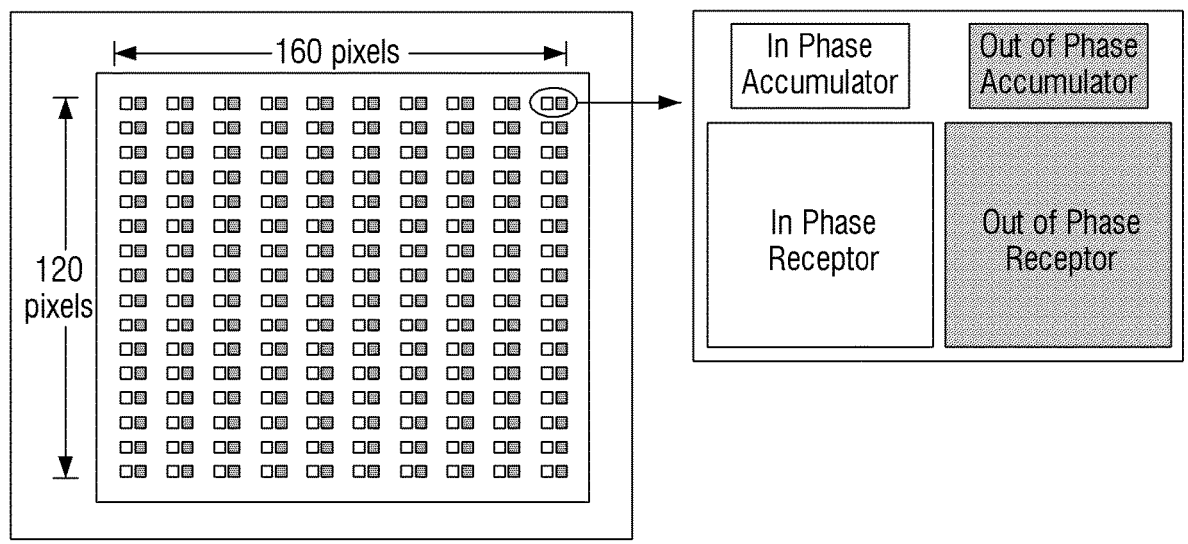
FIG. 3 is a view illustrating a structure of an image sensor, according to an exemplary embodiment.

The image sensor 230 will now be described in more detail. As shown in FIG. 3, two light-receiving parts are paired in each of cells of the image sensor 230. Here, the light-receiving parts may sense the reflected light reflected from the object. Also, the light-receiving parts may include in-phase light-receiving parts and out-phase light-receiving parts. The in-phase light-receiving parts may be activated only in an in-phase status to receive the reflected light, and the out-phase light-receiving parts may be activated only in an out-phase status to receive the reflected light.

The light-emitting device 210, the light-receiving device 220, and the image sensor 230 may be integrated into one sensor module. In particular, as shown in FIG. 2B, the image sensor 230 may be disposed in center of the sensor module, and light-emitting devices 210-1 through 210-4 and light-receiving devices 220-1 through 220-4 may be disposed in a peripheral are of the image sensor 230 and may be paired with each other. Here, the light-emitting devices 210-1 through 210-4 and the light-receiving devices 220-1 through 220-4 make four pairs, but this is only exemplary. The light-emitting devices 210-1 through 210-4 and the light-receiving devices 220-1 through 2204 may make a plurality of pairs. In particular, as the number of light-emitting devices and the number of light-receiving devices increase, volume information of the object may be more precisely acquired.

The transparent display 250 displays various types of user interfaces (UIs) of the body information under control of the controller 240. In detail, the transparent display 250 may display information related to blood flow information such as heart rate information and artery hardening information and information related to volume information such as a body image, weight information, body circumference information, body mass index (BMI) information, etc. of the object. The transparent display 250 may display a content that is received through the communicator 260.

As shown in FIG. 3, the transparent display 250 may be positioned on a front surface of the sensor module. Therefore, the transparent display 250 may transmit the light signal emitted from the light-emitting device 210 of the sensor module and the reflected light reflected from the object.

The transparent display 250 may include a touch sensor. If the transparent display 250 includes the touch sensor, and a hand of a user touches the transparent display 250, the controller 240 may determine that the distance between the light-emitting device 210 and the object is within a first distance.

The transparent display 250 may be positioned on at least one side of a shower booth.

The communicator 260 is an element that communicates with various types of external apparatuses according to various types of communication methods. The communicator 260 may include any of various types of communication chips such as a WiFi chip, a Bluetooth chip, a near field communication (NFC) chip, a wireless communication chip, an IR chip, etc. The WiFi chip, the Bluetooth chip, the NFC chip, and the IR chip respectively perform communications according to a WiFi method, a Bluetooth method, an NFC method, and an IR method. The NFC chip refers to a chip that operates according to an NFC method using a band of 13.56 MHz among various radio frequency identification (RFID) frequency bands such as 135 KHz, 13.56 MHz, 433 MHz, 860-960 MHz, 2.45 GHz, etc. If the WiFi chip or the Bluetooth chip is used, the communicator 260 may transmit and receive various types of connection information such as subsystem identification (SSID), a session key, etc. to perform communication connections by using the various types of connection information and then transmit and receive various types of information. The wireless communication chip refers to a chip that perform communications according to various types of communication standards such as IEEE, Zigbee, $3^{rd}$ Generation (3G), $3^{rd}$ Generation Partnership Project (3GPP), Long Term Evolution (LTE), etc.

In particular, the communicator 260 may transmit the body information sensed under control of the controller 240 to an external display apparatus. The communicator 260 may also transmit control information for controlling an external apparatus to the external apparatus.

The storage unit 270 stores various types of modules for driving the apparatus 200. For example, the storage unit 270 may store software including a base module, a sensing module, a communication module, a presentation module, and a service module. The base module processes signals transmitted from respective pieces of hardware included in the apparatus 200 and transmits the processed signals to an upper layer module. The sensing module collects information from various types of sensors, and analyzes and manages the collected information. The sensor module may also include a face recognition module, a voice recognition module, a motion recognition module, an NFC module, etc. The presentation module constitutes a display screen and may include a multimedia module for playing and outputting a multimedia content and a UI rendering module for processing a UI and a graphic. The communication module communicates with an external source. The service module includes various types of applications for providing various services.

In particular, the storage unit 270 may include a distance information sensing module, a volume information sensing module, and a blood flow information sensing module to acquire the body information of the object.

The controller 240 may control the apparatus 200 by using various types of modules and programs stored in the storage unit 270. In particular, the controller 240 may selectively drive at least one of the light-receiving device 220 and the image sensor 230 according to the distance between the object and the light-emitting device 210 to acquire a reflected light signal and sense volume information or blood flow information of the object by using the reflected light signal.

In detail, the controller 240 may measure the distance between the object and the light-emitting device 210. In particular, in order to measure the distance between the object and the light-emitting device 210, the controller 240 may activate the image sensor 230 to sense the reflected light that is acquired by reflecting the light signal emitted from the light-emitting device 2110 from the object. The controller 240 may also calculate a saturation of the reflected light sensed by the image sensor 230 to measure the distance between the object and the light-emitting device 210. If the saturation is higher than or equal to a preset first value, the controller 240 may determine that the distance between the object and the light-emitting device 210 is within a first distance. The first distance may be a thickness of the transparent display 250. If the saturation is lower than the preset first value and higher than or equal to a preset second value, the controller 240 may determine that the distance between the object and the light-emitting device 210 exceeds the first distance and is within a second distance. The second distance may be 30 cm, but this is only exemplary. Therefore, the second distance may be another value. If the saturation is lower than the preset second value, the controller 240 may determine that the distance between the object and the light-emitting device 210 exceeds the second distance.

As described above, the measurement of the distance between the object and the light-emitting device 210 by using the saturation of the reflected light sensed by the image sensor 230 is only an exemplary embodiment. Therefore, the distance between the object and the light-emitting device 210 may be measured by using other methods. In detail, if a touch of a user's hand on the transparent display 250 is sensed, the controller 240 may determine that the distance between the object and the light-emitting device 210 is within the first distance. In other words, if the touch of the user's hand on the transparent display 250 is sensed, the controller 240 may determine that the distance between the object and the light-emitting device 210 is the first distance that is the thickness of the transparent display 250.

The controller 240 may selectively drive one of the light-receiving device 220 and the image sensor according to the distance between the object and the light-emitting device 210 to sense volume information or blood flow information of the object.

A method of sensing volume information or blood flow information of a user will now be described with reference to FIGS. 4 through 6C.

Figure 4:
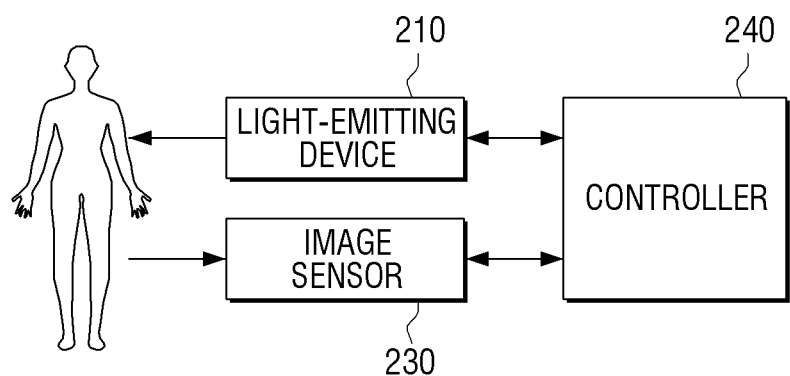
FIG. 4 is a view illustrating a method of acquiring voluptuousness information of a user at a long distance, according to an exemplary embodiment.

FIG. 4 is a view illustrating a method of sensing volume information about a whole area of an object that is to be sensed, according to an exemplary embodiment. If it is determined that a distance between the object and the light-emitting device 210 exceeds a second distance, the controller 240 may drive the light-emitting device 210 and the image sensor 230. Also, the image sensor 230 may detect reflected light that is emitted from the light-emitting device 210 and reflected from the object. The controller 240 may acquire depth data by using the reflected light detected by the image sensor 230. The depth data may be data that expresses the distance between the object and the light-emitting device 210 in a pixel type resolution size. The depth data may be realized as one of 8 bit, 16 bit, and 32 bit types.

The controller 240 may acquire volume information about a whole area (e.g., a whole body of a user) of the object by using the depth data. The volume information about the whole area of the object may include at least one of a whole body image, weight information, body circumference information, and a BMI value of the object.

The controller 240 may control the transparent display 250 to display at least one of the whole body image, the weight information, the body circumference information, and the BMI value of the object and control the communicator 260 to transmit at least one of the whole image, the weight information, the body circumference information, and the BMI value to an external display apparatus.

Figure 5:
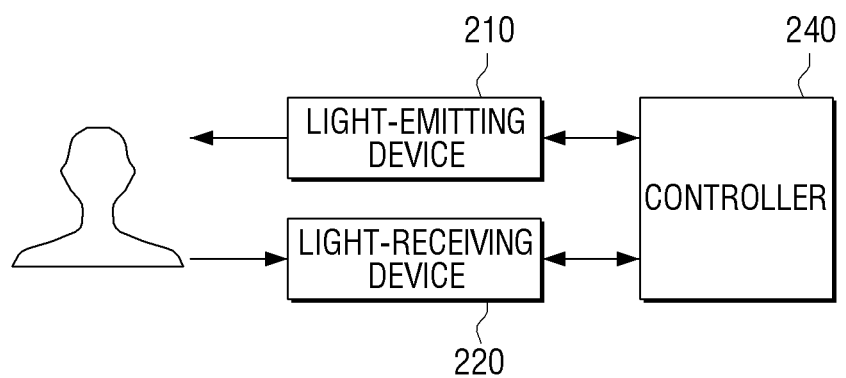
FIG. 5 is a view illustrating a method of acquiring voluptuousness information of a user at a short distance, according to an exemplary embodiment.

FIG. 5 is a view illustrating a method of sensing volume information about an area of an object that is to be sensed, according to an exemplary embodiment. If it is determined that a distance between the object and a light-emitting device 210 exceeds a first distance and is within a second distance, a controller 240 may sequentially drive the light-emitting device 210 and a light-receiving device 220 that is paired with the light-emitting device 210. The light-receiving device 220 may detect reflected light that is emitted from the light-emitting device 210 and reflected from the object. The controller 240 may acquire depth data by using the reflected light detected by the light-receiving device 220 The depth data may be data that expresses the distance between the object and the light-emitting device 210 in a pixel type resolution size and may be realized as one of 8 bit, 16 bit, and 32 bit types.

The controller 240 may acquire volume information about an area of the object (e.g., a whole body of a user) by using the depth data. The volume information about the area of the object may include at least one of an image of an area of a body of the object and body circumference information about the area.

The controller 240 may control the transparent display 250 to display at least one of the image of the area of the body of the object and the body circumference information of the area and control the communicator 260 to transmit at least one of the image of the area of the body of the object and the body circumference information of the area.

Figure 6A:
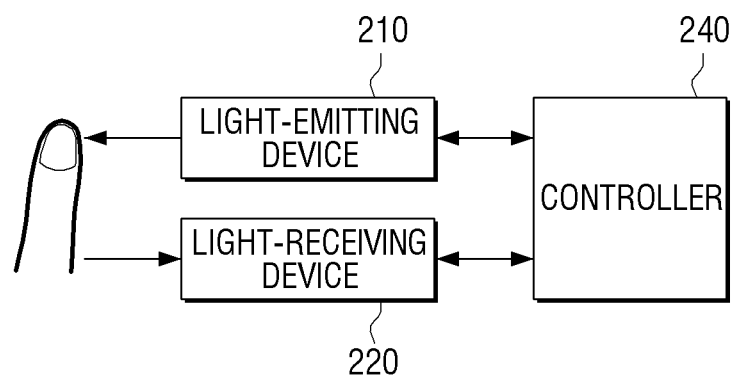
FIGS. 6A through 6C are views illustrating a method of acquiring blood flow information of a user, according to an exemplary embodiment.
Figure 6B:
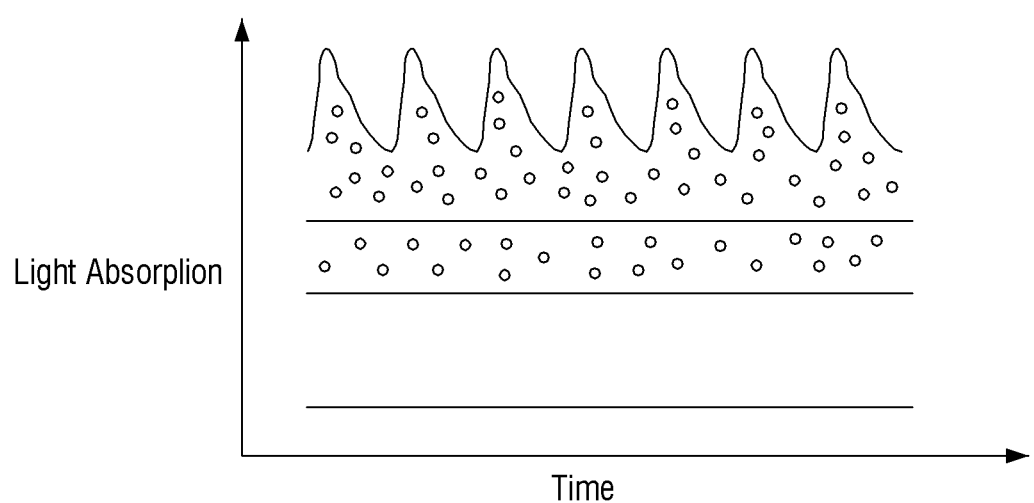
Figure 6C:
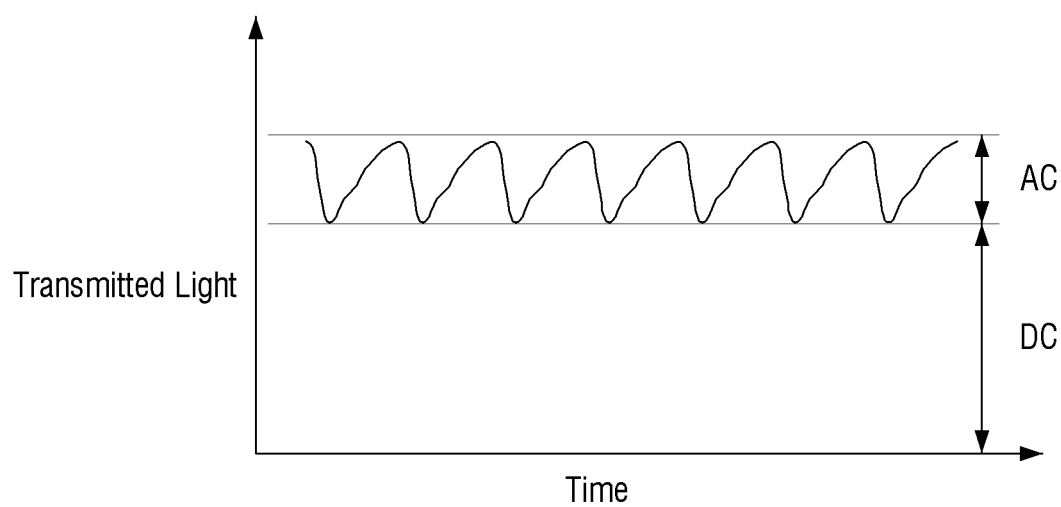

FIGS. 6A through 6C are views illustrating a method of acquiring blood flow information of an object that is to be sensed, according to an exemplary embodiment. If it is determined that a distance between the object and a light-emitting device 210 is within a first distance, the controller 240 may sequentially drive the light-emitting device 210 and a light-receiving device 220 that is paired with the light-emitting device 210. The light-receiving device 220 may detect reflected light that is emitted from the light-emitting may detect reflected light that is emitted from the light-emitting device 210 and reflected from the object (e.g., a finer or the like). The controller 240 may acquire blood flow data by using the reflected light detected by the light-receiving device 220.

In more detail, if the light-emitting device 210 may emit a light signal to a finger of a human, blood, bones, and tissues of the finger absorb light, and a portion of the light may be reflected to be detected by the light-receiving device 22. In particular, an absorption degree of the light is proportional to the skin, tissues, and amount of blood positioned within the path of the light. However, as shown in FIG. 6B, the absorption degree of the light is not changed by other components except a blood flow change caused by a heart rate.

Therefore, as shown in FIG. 6C, the light-receiving device 220 may receive the reflected light from which an amount corresponding to a light amount absorbed into the finger is subtracted. Therefore, a light amount change of the reflected light may also indicate the blood flow change, and thus the light-receiving device 220 may measure an amount of the reflected light to detect a blood volume change synchronizing with the heart rate. In particular, component AC shown in FIG. 6C is generally referred to as a Photo PlethysmoGraph (PPG).

Blood flow data may be realized as one of 8 bit, 16 bit, and 32 bit types and may be constituted along with or separately from depth data.

The controller 240 may acquire blood flow information of the object by using the blood flow data. Blood flow information may include heart rate information and artery hardening information.

The controller 240 may control the transparent display 250 to display at least one of the heart rate information and the artery hardening information and control the communicator 260 to transmit at least one of the heart rate information and the artery hardening information to the external display apparatus. The heart rate information may be displayed as a numerical value, but this is only exemplary. Therefore, the heart rate information may be displayed in a graph form.

Figure 7A:
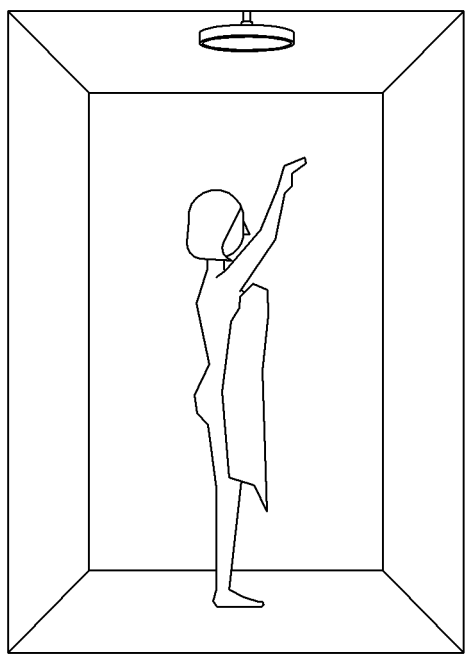
FIGS. 7A and 7B are views illustrating a process of displaying body information of a user, according to an exemplary embodiment.

The apparatus 200 according to the present exemplary embodiment may be installed in a shower booth, and at least one side of the shower booth may be realized as the transparent display 250. In detail, as shown in FIG. 7A, the apparatus 200 may be installed in three sides of the shower booth, and the three sides of the shower booth may be realized as the transparent display 250.

Figure 7B:
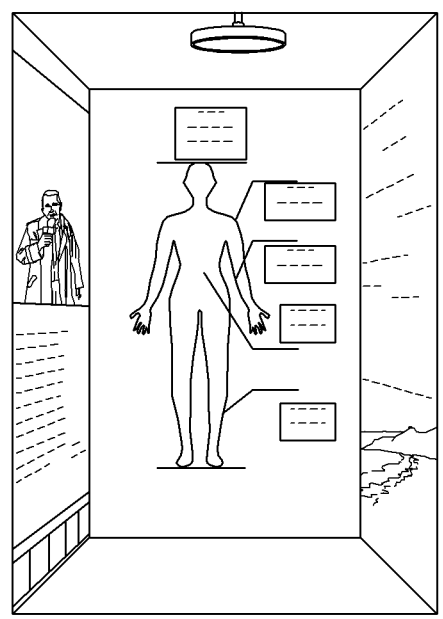

Here, the apparatus 200 installed on at least one side of the shower booth may acquire body information (a whole body image, a BMI value, heart rate information, artery hardening information, etc.) of a user according to a method as described above and display the body information on a side of the shower booth as shown in FIG. 7B. The apparatus 200 may display contents, which are received from an external source, on another side of the shower booth and display an image content stored in the storage unit 270.

In the above-described exemplary embodiment, the controller 240 selectively drives one of the light-receiving device 220 and the image sensor 230 according to the distance between the object and the light-emitting device 210 to sense one of volume information and blood flow information. However, this is only an exemplary embodiment, and the controller 240 may sense one of the volume information and the blood flow information according to another method.

In detail, the controller 240 may selectively operate in one of a first operation mode for sensing blood flow information of the object by using the light-receiving device 220, a second operation mode for sensing volume information of the object by using the light-receiving device 220, and a third operation mode for sensing the volume information of the object by using the image sensor 230. The first, second, and third operation modes may be set according to a user input. The user input may be input through various types of input devices such as a touch screen, a remote controller, a pointing device, a voice input device, a motion input device, etc.

In detail, if the first operation mode is set by the user input, the controller 240 may sequentially drive a plurality of light-emitting devices 210 to emit light signals and sequentially drive a plurality of light-receiving devices 220 to emit reflected light reflected from the object in order to sense blood flow information of the object. Also, if the second operation mode is set by the user input, the controller 240 may sequentially drive the plurality of light-emitting devices 210 to emit the light signals and sequentially drive the plurality of light-receiving devices 220 to detect the reflected light reflected from the object in order to sense volume information about an area of the object. If the third operation mode is set by the input unit, the controller 240 may drive the light-emitting device 210 to emit a light signal and drive the image sensor to detect reflected light reflected from the object in order to sense volume information about a whole area of the object. If the third operation mode is set, and a distance between the object and the light-emitting device 210 is within a preset second distance, the controller 240 may control the transparent display 250 to determine that a saturation of the reflected light is higher than or equal to a preset value in order to display a notification message about that the volume information about the whole area of the object may not be sensed. Also, the controller 240 may automatically convert an operation mode into the second operation mode to sense the volume information about the area of the object.

In the above-described exemplary embodiment, the transparent display 250 is used to display various types of body information, but this is only exemplary. The transparent display 250 may be realized as other types of displays (e.g., a cathode ray tube (CRT), a liquid crystal display (LCD), an organic light-emitting diode (OLED), etc.)

The user may simultaneously acquire blood flow information and volume information of the user by using the apparatus 200 for sensing the body information as described above and thus systematically manage health.

Figure 8:
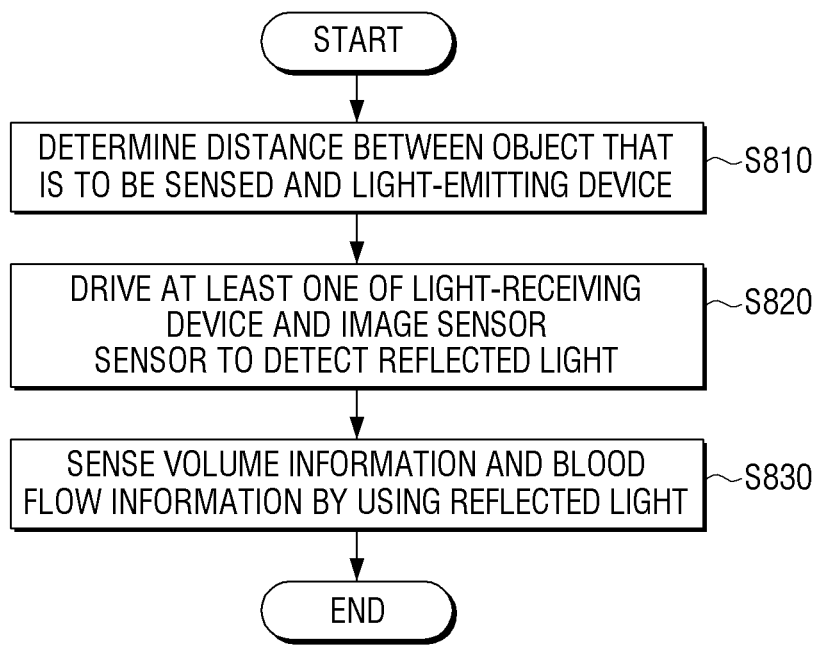
FIG. 8 is a flowchart briefly illustrating a method of sensing body information, according to an exemplary embodiment.

Methods of sensing body information according to exemplary embodiments concept will now be described with reference to FIGS. 8 and 9. FIG. 8 is a flowchart of a method of sensing body information through the apparatus 200 for sensing body information, according to an exemplary embodiment.

Referring to FIG. 8, in operation S810, the apparatus 200 determines a distance between an object that is to be sensed and the light-emitting device 210. The apparatus 200 may drive the image sensor 230 to determine the distance between the object and the light-emitting device 210 by using a saturation of reflected light reflected from the object. The apparatus 200 may also determine the distance between the object and the light-emitting device 210 by using a user touch input into the transparent display 250.

In operation S820, the apparatus 200 drives at least one of the light-receiving device 220 and the image sensor 230 to detect the reflected light. In detail, if it is determined that the distance between the object and the light-emitting device 210 is within a second distance, the apparatus 200 may detect the reflected light by using the light-receiving device 220. If it is determined that the distance between the object and the light-emitting device 210 exceeds the second distance, the apparatus 200 may detect the reflected light by using the image sensor 230.

In operation S830, the apparatus 200 senses volume information or blood flow information by using the acquired reflected light. In detail, if it is determined that the distance between the object and the light-emitting device 210 is within a first distance, the apparatus 200 may sense the blood flow information by using the reflected light detected by the light-receiving device 220. Also, if it is determined that the distance between the object and the light-emitting device 210 exceeds the first distance and is within the second distance, the apparatus 200 may sense volume information about an area of the object by using the reflected light detected by the light-receiving device 220. If it is determined that the distance between the object and the light-emitting device 210 exceeds the second distance, the apparatus 200 may sense volume information about a whole area of the object by using the reflected light detected by the image sensor 230.

Figure 9:
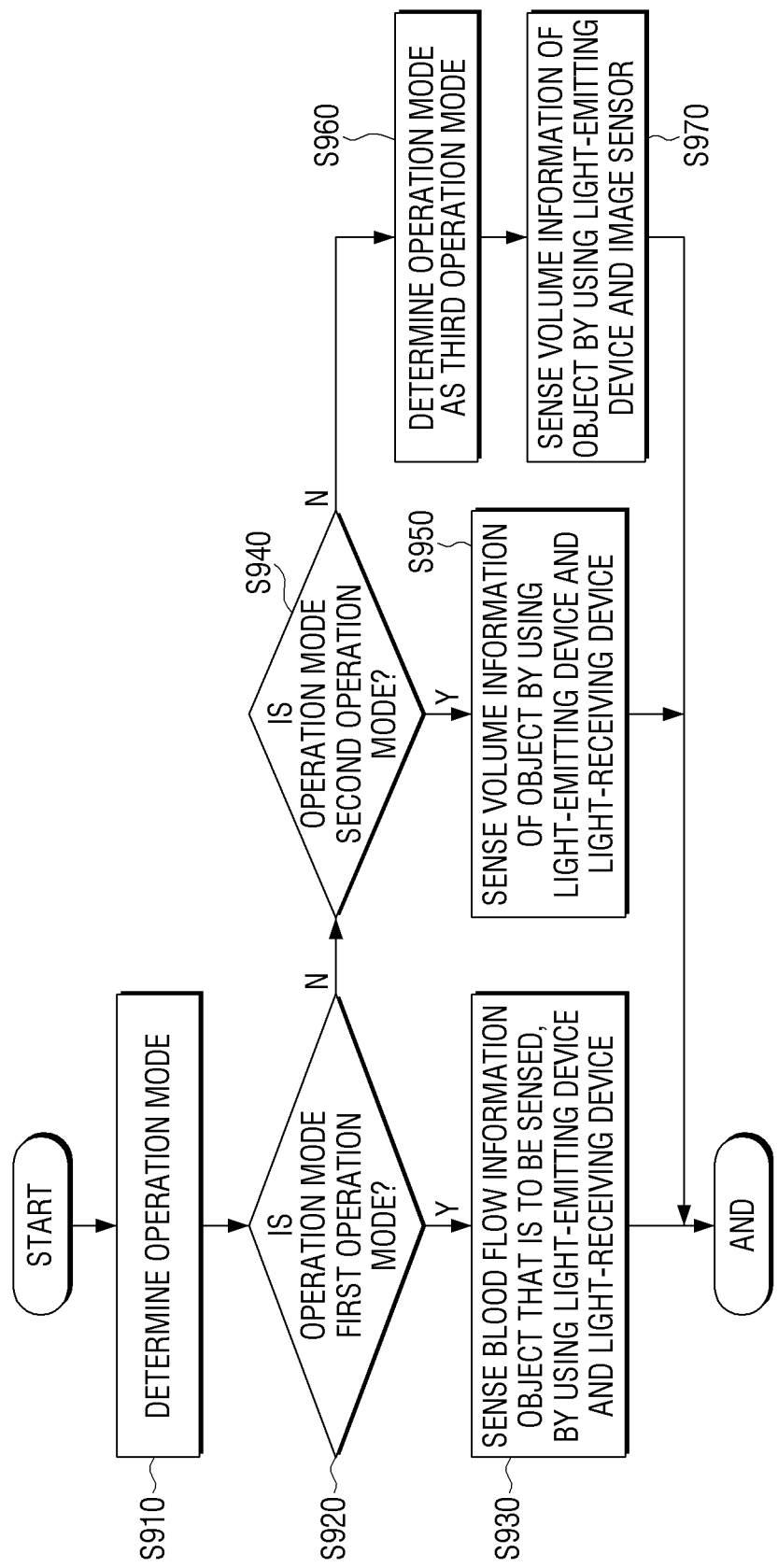
FIG. 9 is a flowchart illustrating a method of sensing body information, according to another exemplary embodiment.

FIG. 9 is a flowchart of a method of sensing body information through the apparatus 200 for sensing body information, according to another exemplary embodiment.

Referring to FIG. 9, in operation S910, the apparatus 200 determines an operation mode. The operation mode of the apparatus 200 may be set by a user input.

If it is determined in operation S920 that the operation mode of the apparatus 200 is a first operation mode, the apparatus 200 blood flow information of an object that is to be sensed, by using the light-emitting device 210 and the light-receiving device 220 in operation S930.

If it is determined in operation S940 that the operation mode of the apparatus 200 is a second operation mode, the apparatus 200 senses volume information of the object by using the light-emitting device 210 and the light-receiving device 220 in operation S950. The apparatus 200 may sense volume information about an area of the object by using the light-emitting device 210 and the light-receiving device 220.

If it is determined in operations S920 and S940 that the operation mode of the apparatus 200 is not the first operation mode and the second operation mode, the apparatus 200 determines that the operation mode is a third operation mode in operation S960 and senses the volume information of the object by using light-emitting device 210 and the image sensor 230 in operation S970. The apparatus 200 may sense volume information about a whole area of the object by using the light-emitting device 210 and the image sensor 230.

As described with reference to FIGS. 8 and 9, one of the light-receiving device 220 and the image sensor 230 may be selectively driven to acquire reflected light in order to simultaneously acquire volume information and blood flow information of the object.

In the above-described exemplary embodiment, the distance between the object and the light-emitting device 210 is determined by using the saturation of the reflected light detected by the image sensor 230. However, this is only exemplary: the apparatus 200 may determine the distance between the object and the light-emitting device 210 by using other methods.

Figure 10:
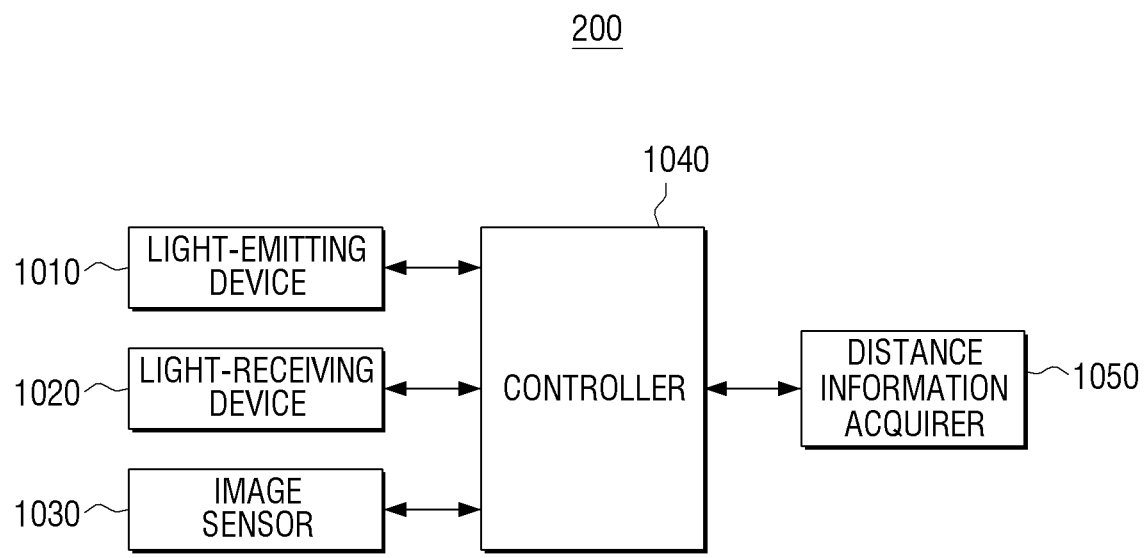
FIG. 10 is a block diagram illustrating a structure of an apparatus for sensing body information, according to another exemplary embodiment.

In detail, as shown in FIG. 10, the apparatus 200 for sensing the body information may include a light-emitting device 1010, a light-receiving device 1020, an image sensor 1030, a controller 1040, and a distance information acquirer 1050. The descriptions of the light-emitting device 1010, the light-receiving device 1020, and the image sensor 1030 are the same as those of the light-emitting device 110, the light-receiving device 120, and the image sensor 130 of FIG. 1, and thus their repeated descriptions are omitted herein.

The distance information acquirer 1050 acquires distance information between an object that is to be sensed and the light-emitting device 1010. In detail, the distance information acquirer 1050 may be realized as a sensor for acquiring the distance information between the object and the light-emitting device 1010, i.e., as an ultrasonic sensor or the like. According to another exemplary embodiment, the distance information acquirer 1050 may acquire the distance information between the object and the light-emitting device 1010 through a direct input of a user.

The controller 1040 may selectively drive at least one of the light-receiving device 1020 and the image sensor 1030 according to the distance between the object and the light-emitting device 1010 to acquire a reflected light signal, wherein the distance is acquired by the distance information acquirer 1050. The controller 1040 may also sense volume information or blood flow information of the object by using the reflected light signal.

Figure 11:
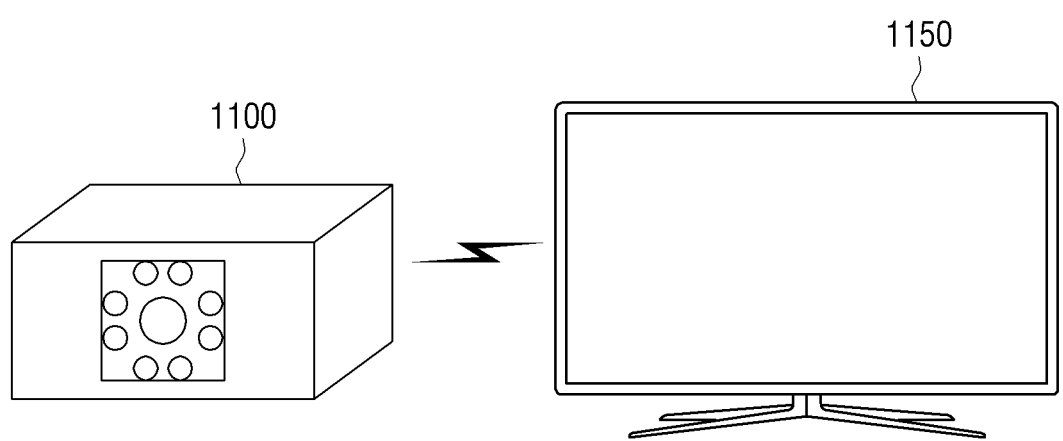
FIGS. 11 and 12 are views illustrating a process of displaying body information, which is sensed by an apparatus for sensing body information, on an external display apparatus, according to an exemplary embodiment.

According to an exemplary embodiment, an apparatus 1100 for sensing body information may not include an additional display unit but may display body information by using an external display apparatus 1150 as shown in FIG. 11.

Figure 12:
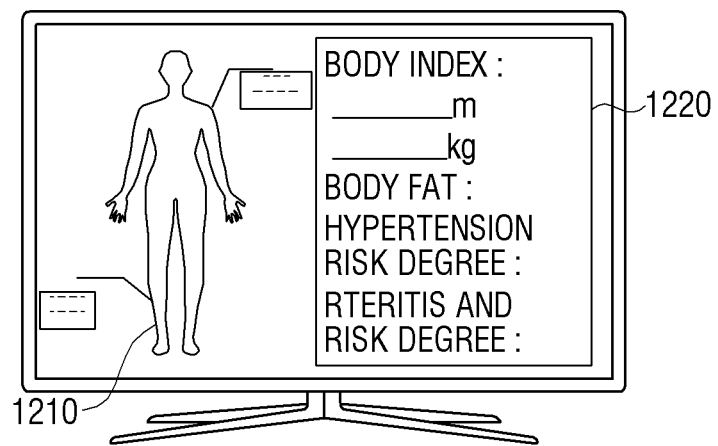

In detail, as shown in FIGS. 2A through 6C, the apparatus 1100 may sense volume information or blood flow information. The apparatus 1100 may transmit the sensed volume information or blood flow information to the external display apparatus 1155 by using a communicator using a wired communication method or a wireless communication method. The external display apparatus 1150 may provide various types of user interfaces (UIs) by using the volume information or the blood flow information. For example, as shown in FIG. 12, the external display apparatus 1150 may display a body image UI 1210 of an object that is to be sensed and a body information UI 1220 including various types of body information.

Figure 13:
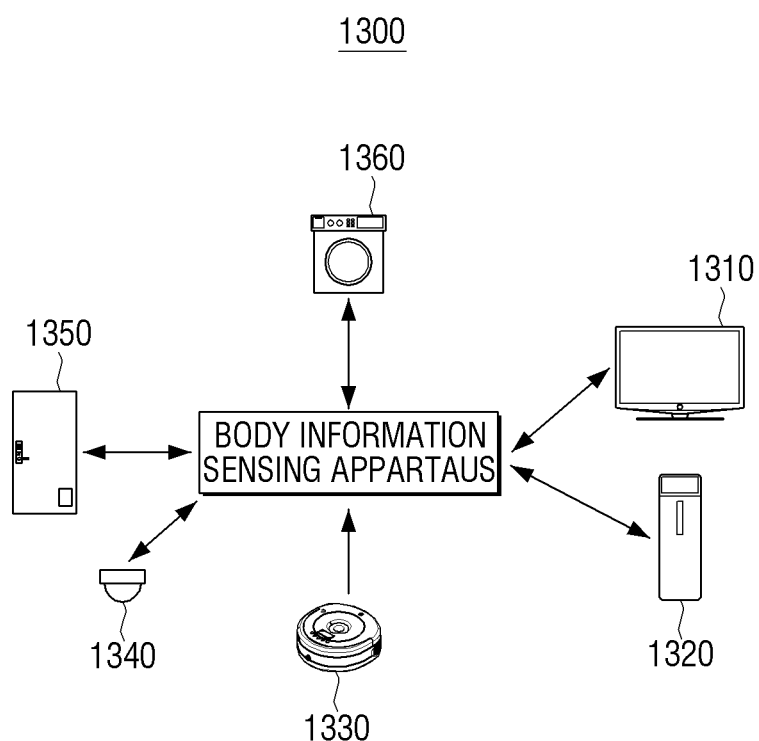
FIGS. 13 and 14 are a view and a flowchart illustrating a method of acquiring motion information of a user through an apparatus for sensing body information to control an external apparatus, according to an exemplary embodiment.

According to another exemplary embodiment, the apparatus 100 for sensing the body information may sense a motion of a user and control an external apparatus by using a body image of volume information. In detail, a home control system 1300 may include a body information sensing apparatus 200, a TV 1310, an air conditioner 1320, a vacuum cleaner 1330, an illumination lamp 1340, a front door 1350, and a washing machine 1360. The home control system 1300 may include other types of devices besides devices used in a home as shown in FIG. 13.

The body information sensing apparatus 200 may acquire a body image of an area of the object by using the light-emitting device 210 and the light-receiving device 220 and sense a user motion by using the body image. The body information sensing apparatus 200 may determine a control command by using the sensed user motion and transmit the control command corresponding to the user motion to a device that is to be controlled.

As described above, the body information sensing apparatus 200 may sense the user motion by using the light-emitting device 210 and the light-receiving device 220 to control various types of devices that are to be controlled. For example, the body information sensing apparatus 200 may perform various types of controls, such as controls of power, a volume, a channel, etc. of the TV 1310, by using the sensed user motion. The body information sensing apparatus 200 may perform various types of controls such as controls of wind, wind strength, a wind direction, etc. of the air conditioner 1320 by using the sensed user motion. The body information sensing apparatus 200 may perform various types of controls, such as controls of power, inhaling strength, etc. of the vacuum cleaner 1330, by using the sensed user motion. The body information sensing apparatus 200 may also perform various types of controls, such as controls of power, brightness, etc. of the illumination lamp 1340, by using the sensed user motion. The body information sensing apparatus 200 may perform a control for opening and closing the front door 1350 by using the sensed user motion. The body information sensing apparatus 200 may perform various types of controls, such as power, an operation mode, etc. of the washing machine 1360, by using the sensed user motion. External devices as described above are only exemplary, and other types of external devices may be controlled by using a user motion.

Figure 14:
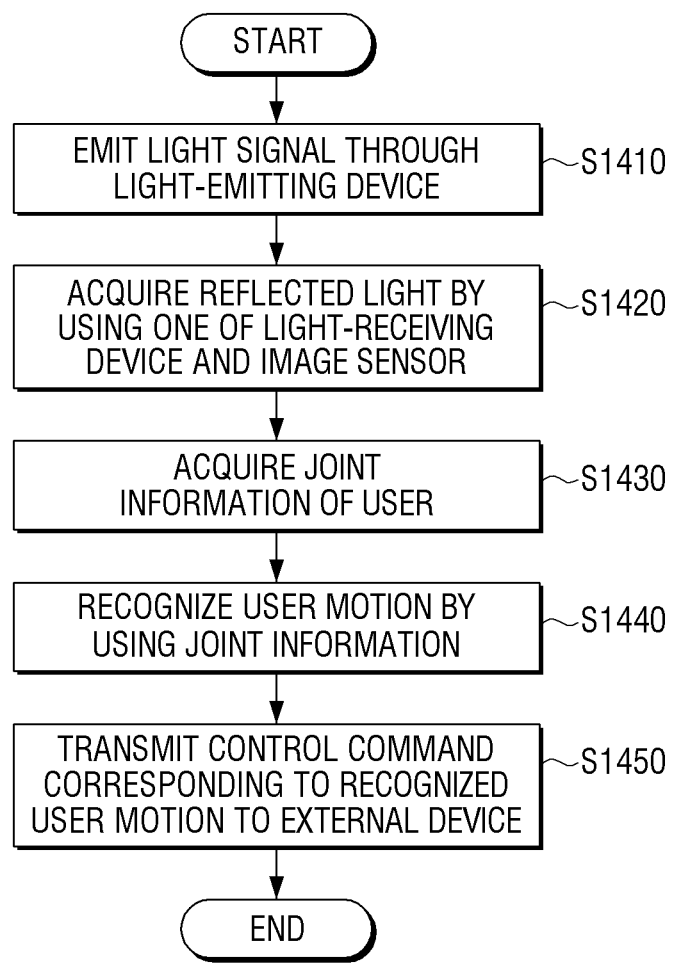

FIG. 14 is a flowchart of a method of sensing a user motion by using the body information sensing apparatus 200 to control an external device, according to an exemplary embodiment.

Referring to FIG. 14, in operation S1410, the body information sensing apparatus 200 emits a light signal through the light-emitting device 210.

In operation S1420, the body information sensing apparatus 200 acquires reflected light reflected from a user by using one of the light-receiving device 220 and the image sensor 230. In particular, the body information sensing apparatus 200 may acquire the reflected light reflected from an object that is to be sensed, by using the light-receiving device 220 in order to sense a motion of an area of a body of the user.

In operation S1430, the body information sensing apparatus 200 acquires joint information of the user. In detail, the body information sensing apparatus 200 may acquire a body image by using the acquired reflected light. The body information sensing apparatus 200 may acquire a joint area of the user by using the acquired body image.

In operation S1440, the body information sensing apparatus 200 recognizes a user motion by using the joint information. In detail, the body information sensing apparatus 200 may connect a plurality of joint areas to one another to acquire line. The body information sensing apparatus 200 may recognize the user motion by using a movement direction of the light and an increase or a decrease in a length of the line.

In operation S1450, the body information sensing apparatus 200 transmits a control command corresponding to the recognized user motion to an external device. In detail, the body information sensing apparatus 200 may generate a control command corresponding to an external device that is to be controlled, by using user motion information and transmit the generated control command to the external device.

A method of transmitting body information sensed by a body information sensing apparatus to an external service to provide a body management service to a user according to an exemplary embodiment will now be described with reference to FIGS. 15 and 16.

Figure 15:
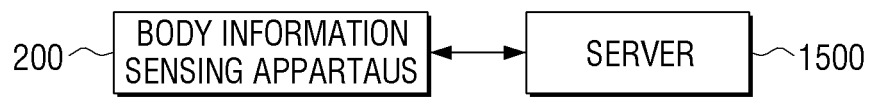
FIGS. 15 and 16 are views illustrating a process of transmitting body information, which is sensed by an apparatus for sensing body information, to an external service to provide a body management service to a user, according to an exemplary embodiment.

As shown in FIG. 15, a system for providing a body management service includes a body information sensing apparatus 200 and a server 1500. In detail, the body information sensing apparatus 200 may acquire various types of body information such as blood flow information, volume information, etc. according to methods as described above and transmit the acquired body information to the server 1500.

The server 1500 may store the received body information in a database (DB) and analyze the body information. If an unusual symptom is detected from a body of a user according to the analysis result of the body information, the server 1500 may transmit the analysis result including information about the unusual symptom to the body information sensing apparatus 200. The body information sensing apparatus 200 may display the analysis result, and the user may check the analysis result to check a health status of the user. The server 1500 may transmit the analysis result of the body information to a terminal of a hospital that the user frequently goes to.

Figure 16:
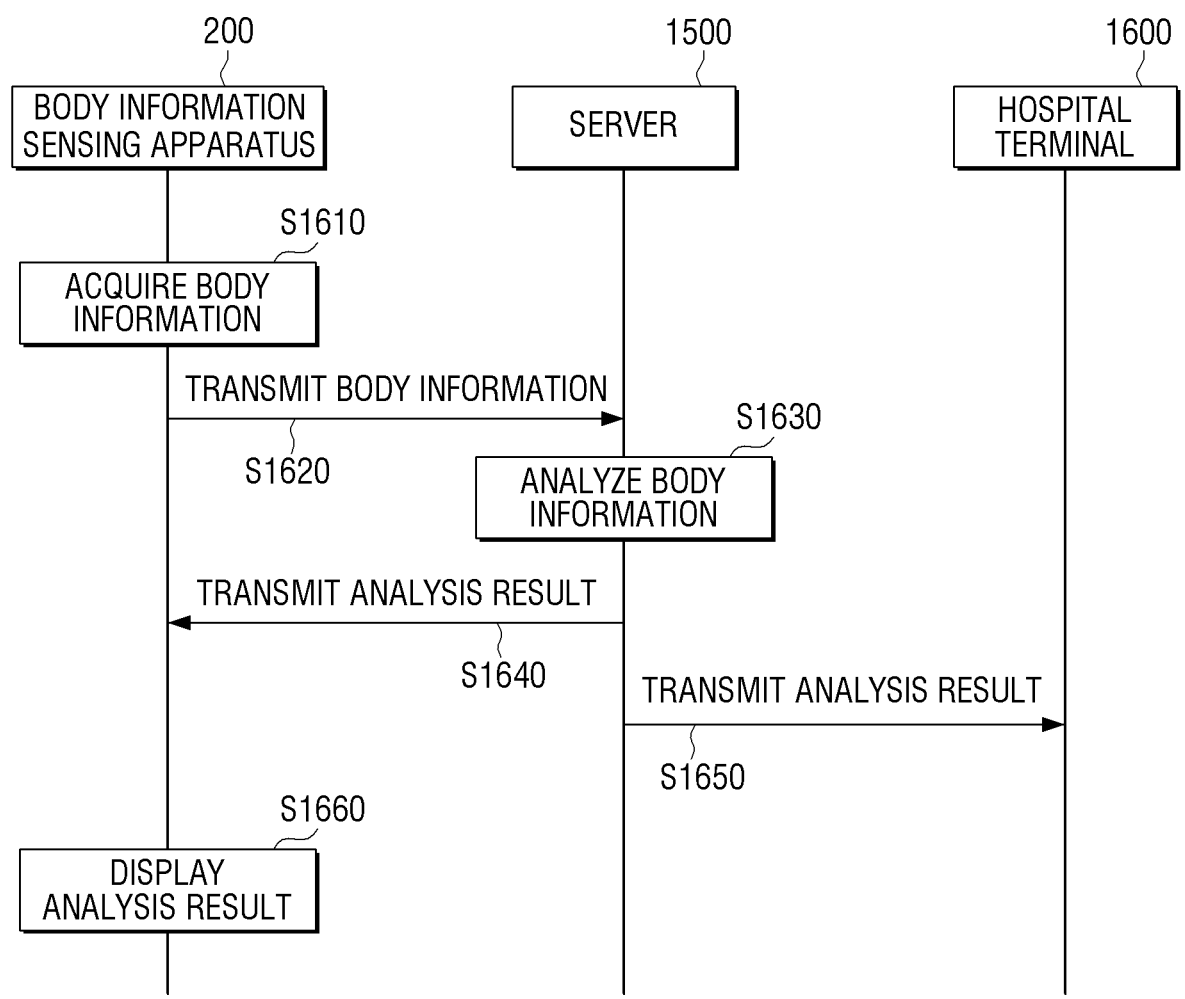

FIG. 16 is a sequence chart illustrating a method of transmitting body information sensed by the body information sensing apparatus 200 to an external server to provide a body management service to a user, according to an exemplary embodiment.

In operation S1610, the body information sensing apparatus 200 acquires body information. In detail, the body information sensing apparatus 200 may selectively drive at least one of the light-receiving device 220 and the image sensor 230 according to a distance between an object that is to be sensed and the light-emitting device to acquire a reflected light signal and acquire volume information or blood flow information of the object by using the reflected light signal.

In operation S1620, the body information sensing apparatus 200 transmits the acquired body information to the server 1500.

In operation S1630, the server 1500 analyzes the received body information. The server 1500 may analyze an unusual symptom of a body of a user by using the body information. In detail, the server 1500 may analyze unusual symptoms of heart and blood vessels of the user by using the blood flow information and analyze an unusual symptom of a sudden body change of the user by using depth information.

In operations S1640 and S1650, the server 1500 transmits the analysis result to the body information sensing apparatus 200 and a hospital terminal 1600. The server 1500 may periodically transmit the analysis result to the body information sensing apparatus 200 and the hospital terminal 1600, but this is only exemplary. However, if an unusual symptom is sensed, the server 1500 may transmit the analysis result to the body information sensing apparatus 200 and the hospital terminal 1600.

In operation S1660, the body information sensing apparatus 200 displays the received analysis result.

As described above, the server 1500 may analyze body information and provide the analysis result to a user. Therefore, the user may be provided with a systematic and specialized health management service.

A method of sensing body information according to various exemplary embodiments as described above may be embodied as a program and then provided to a display apparatus or an input device. In particular, a program including a method of controlling the display apparatus may be stored and provided on a non-transitory computer-readable medium.

The non-transitory computer-readable medium refers to a medium which does not store data for a short time such as a register, a cache memory, a memory, or the like but semi-permanently stores data and is readable by a device. In detail, the above-described various applications or programs may be stored and provided on a non-transitory computer readable medium such as a CD, a DVD, a hard disk, a blue-ray disk, a universal serial bus (USB), a memory card, a ROM, or the like.

The foregoing exemplary embodiments and advantages are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for sensing body information, the apparatus comprising:
   a light-emitting device configured to emit light toward an object;
   a light-receiving device;

an image sensor; and a controller configured to:

determine a distance between the object and the light-emitting device;

selectively drive, based on the distance between the object and the light-emitting device, at least one of the light-receiving device and the image sensor to detect reflected light reflected from the object; and determine volume information about an area or a whole area of the object and blood flow information of the object based on the reflected light, wherein the controller is configured to determine, using the reflected light detected by the light-receiving device, the blood flow information of the object based on determining that the distance between the object and the light-emitting device is less than a first distance, wherein the controller is configured to, based on determining that the distance between the object and the light-emitting device is greater than the first distance, determine the volume information about the area of the object using the reflected light detected by the light-receiving device or determine the volume information about the whole area of the object using the reflected light detected by the image sensor, and wherein the controller is configured to, when the distance between the object and the light-emitting device exceeds the first distance and is within a second distance, determine the volume information about the area of the object using the reflected light detected by the light-receiving device, and when the distance between the object and the light-emitting device exceeds the first distance and the second distance, determine the volume information about the whole area of the object using the reflected light detected by the image sensor.

2. The apparatus of claim 1, wherein the controller is configured to activate the image sensor to sense a saturation of the reflected light and selectively drive the at least one of the light-receiving device and the image sensor according to an amount of the saturation, wherein the saturation varies according to the distance between the object and the light-emitting device.

3. The apparatus of claim 2, wherein the light-emitting device, the light-receiving device, and the image sensor are integrated into a single sensor module, wherein the image sensor is disposed in a center of the sensor module, the light-emitting device comprises a plurality of light-emitting devices disposed in a peripheral area of the image sensor, the light-receiving device comprises a plurality of light-receiving devices disposed in conjunction with the plurality of light-emitting devices, and each of the plurality of light-receiving devices is paired with one of the plurality of light-emitting devices.

4. The apparatus of claim 3, further comprising:

a transparent display configured to cover the sensor module, and to transmit the light emitted from the light-emitting device and the reflected light reflected from the object, wherein the controller is configured to control the transparent display to display at least one of the blood flow information and the volume information.

5. The apparatus of claim 4, wherein the blood flow information comprises heart rate information and artery hardening information, and the volume information comprises at least one of a body image, weight information, body circumference information, and a body mass index (BMI) value of the object, wherein the controller is configured to control the transparent display to display at least one of the heart rate information, the artery hardening information, the body image, the weight information, the body circumference information, and the BMI value of the object.

6. The apparatus of claim 4, wherein the controller is configured to, in response to a user touching the transparent display, determine that the distance between the object and the light-emitting device is within the first distance.

7. The apparatus of claim 1, further comprising:

a communicator configured to communicate with an external display apparatus, wherein the controller is configured to control the communicator to transmit at least one of the volume information and the blood flow information to the external display apparatus.

* * * * *